United States Patent [19]

Bresak et al.

[11] 4,452,261
[45] Jun. 5, 1984

[54] HAIR SETTING COMPOSITION AND METHOD

[75] Inventors: Ann F. Bresak; Eva Tolgyesi, both of Rockville, Md.

[73] Assignee: The Gillette Company, Boston, Mass.

[21] Appl. No.: 344,090

[22] Filed: Jan. 29, 1982

[51] Int. Cl.$^3$ .................. A45D 19/00; A61K 7/11
[52] U.S. Cl. ........................................ 132/7; 424/71
[58] Field of Search ............... 424/71, DIG. 2; 132/7

[56] References Cited

U.S. PATENT DOCUMENTS

| | | | |
|---|---|---|---|
| 3,117,105 | 1/1965 | Borchert | 528/165 |
| 3,479,427 | 11/1969 | Lieberman et al. | 424/47 |
| 4,278,659 | 7/1982 | Breuer | 424/71 |

Primary Examiner—Jerome D. Goldberg
Assistant Examiner—John W. Rollins
Attorney, Agent, or Firm—Leonard J. Janowski

[57] ABSTRACT

This invention deals with compositions for and a method of imparting temporary set to human hair involving the application of an aqueous composition containing a dialdehyde polysaccharide and a hydroxyaromatic compound in which two hydroxyl groups are meta to each other. After application of the composition, the tress is wrapped and heated using a conventional heated rod or brush type curling iron, heated roller, or salon or handheld hot air blower hair dryer to cause the polysaccharide and hydroxyaromatic compound to react with one another.

5 Claims, No Drawings

HAIR SETTING COMPOSITION AND METHOD

BACKGROUND

This invention deals with compositions for and a method of imparting temporary set to human hair involving the application of an aqueous composition containing a dialdehyde polysaccharide and a hydroxyaromatic compound in which two hydroxyl groups are meta to each other. After application of the composition to the hair, the tress is wrapped and heated using a conventional heated rod or brush type curling iron, heated roller, or salon or hand-held hot air blower hair dryer to cause the polysaccharide and hydroxyaromatic compound to react with one another.

Since time immemorial, man has exhibited a desire to control the configuration of the hair of the head, exemplified most basically by the daily ritual of combing, which is almost universally practiced. As part of the ritual of hair styling, man has not only come to cut and arrange the hair in styles influenced by the views of society, but has had a continuing desire to be able to either permanently or temporarily alter the hair type genetically bestowed by changing the natural curvature of his hair.

The type of hair configuration bestowed by nature, be it straight, curly, or somewhere in between, is a function of the structure of the hair keratin in which both covalent disulfide bonds and secondary bonds including hydrogen bonds and salt linkages act to maintain the natural fiber configuration.

One way of permanently overcoming the effects of these bonds is to break them by the application of an aqueous reducing agent after which the fibers are arranged in an altered configuration and the disulfide linkages are rebuilt at new sites within the fiber. The end result is a molecular structure in which the covalent bonds serve to maintain a modified hair style. This chemical approach to the problem is the basis for the various "permanent waving" processes and products available for self-application or as beauty shop treatments.

While reductive processes do indeed provide a more or less permanent change in the natural hair configuration, their very permanence tends to render them undesirable in the views of many people. Such people, while wishing to be able to change the natural hair configuration, prefer a means of being able to do so only temporarily and without the bother of subjecting their hair to reductive chemical reaction.

The simplest and probably the oldest method of temporarily altering the natural configuration of hair on the human head is to wet it with water, arrange the fibers in an altered configuration, allow the hair to dry, and then comb it into a desired final style. The temporary nature of water setting is due to the fact that while the secondary bonds, especially the hydrogen bonds, are broken and reformed in the presence of water, the covalent bonds are not. A disadvantage of water setting is that in the presence of a moist atmosphere, as on a humid day or as the result of scalp perspiration, a water-set hair fiber will tend to return to its original configuration by virtue of the influence of the covalent bonds in the keratin.

While the origins of the practice are lost in history, attempts have long been made to use mechanical means to reduce the tendency of hair to revert to its natural form in humid circumstances. While such materials as mud and various naturally occuring gums and resins were used in ancient times to reinforce artificially constructed hair styles, modern man usually applies a solution of oils, waxes, and/or synthetic polymers which serve to mechanically fix the fiber array by partially coating the fiber surfaces and forming interfiber bridges. Since products of this type do not react chemically with the hair keratin to which they are applied, they may be used as often as desired without causing damage.

Inspired by advances in polymer chemistry, investigators have proposed that fibers, including hair, be treated with compositions containing a variety of polymerizable monomeric species under conditions such that polymerization of the species will take place at the surface of or within the hair fiber resulting in the formation of a hair setting polymer film or deposit. Such films and deposits have a degree of semi-permanence not only because they resist water removal, but also because of limited chemical interaction with the fiber surface itself. In spite of this, they can sometimes be removed by conventional shampooing procedures and hence should be considered as improved "temporary" setting agents rather than "permanent" setting agents.

As mentioned above, the practice of this invention involves the use of aqueous compositions containing polymerizable dialdehyde polysaccharides and meta-hydroxyaromatic compounds. A number of investigators have attempted to exploit dialdehyde polysaccharides and a variety of condensation systems in the treatment of natural fibers. This technology is exemplified in the following patents.

U.S. Pat. No. 2,552,130 describes the treatment of wool and animal hair by immersion at room temperature in dilute aqueous solutions of specified polyhydric phenols and nonpolymeric aldehydes to form condensation products on the surface of the fibers to improve body and luster.

U.S. Pat. No. 3,117,105 discloses reaction products of dialdehyde polysaccharides and phenols including meta and para substituted phenols and employing a condensation catalyst to yield polymeric products useful is resins and adhesives formulations.

U.S. Pat. No. 3,479,128 discloses a process for increasing the tensile strength of wool and silk fibers by contact with an aqueous dispersion of a dialdehyde polysaccharide at 20°-40° C.

U.S. Pat. No. 3,584,992 describes a process for modifying wool by reacting it with an anhydrous mixture of cresol and paraformaldehyde at 60°-180° C.

U.S. Pat. No. 3,479,427 discloses hair setting compositions containing hydrated dialdehyde starches.

U.S. Pat. No. 4,278,659 describes hair treatments employing mixtures of glyceraldehyde, resorcinol, and precondensates thereof.

DETAILED DESCRIPTION OF THE INVENTION

In practicing the present invention, human hair is contacted with an aqueous dispersion of a dialdehyde polysaccharide and a meta-hydroxyaromatic compound followed by the application of heat to form a fiber-dialdehyde polysaccharidehydroxyaromatic reaction product.

Dialdehyde polysaccharides are readily obtained by oxidation of polysaccharides such as corn, wheat, or other starches, celluloses, dextrins, dextrans, and the like with periodic acid. This is a well known method for the preparation of dialdehyde polysaccharides and may be illustrated by means of the following equation.

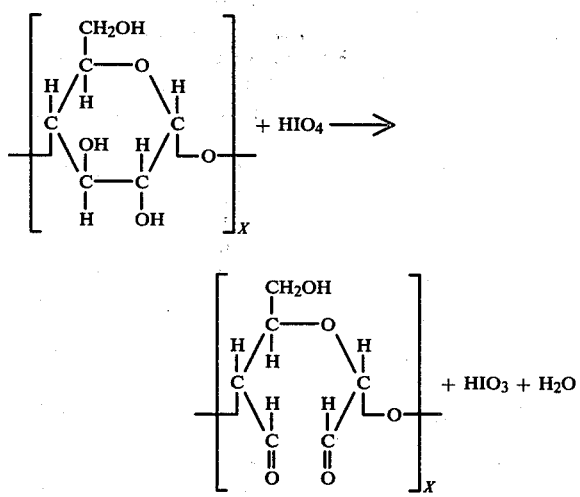

where $\chi$ represents the number of repeating polymer units. More recently electrolytic procedures have been used such as those exemplified by U.S. Pat. No. 2,648,629 to William Drench and Charles L. Mehltretter and U.S. Pat. No. 2,713,553, 2,770,589 and 2,830,941 to Charles L. Mehltretter. Such oxidized polymers for use in this invention may have molecular weights of from about 10,000 to about 500,000.

The preferred dialdehyde polysaccharide for use in the practice of this invention is a dialdehyde starch derived from cornstarch in which from 80–100% of the original anhydrogelucose units have been converted to the dialdehyde form.

Dialdehyde polysaccharides as prepared by the above oxidation techniques must first be hydrated to convert them to a form usable in the practice of this invention. The technique of hydrating natural polysaccharides such as starch is well known in the art and is adapted as well to the hydration of dialdehyde polysaccharides. Hydration is effected by heating an aqueous dispersion of the material to at least 60° C. for a sufficient time to attain a substantially clear solution. The end point is readily determined by visual observation since the dispersion during the heat treating step proceeds to thicken and then becomes substantially thinner at about the time the clarification occurs. For best results and for the purpose of reducing the time required for hydration, it is desirable to add an alkaline material such as sodium bicarbonate or borax at a concentration of about 5 to 15% by weight of the dialdehyde polysaccharide. In such case, hydration will usually take place within 10 to 20 minutes.

As mentioned above, dialdehyde polysaccharides including dialdehyde starches have in the past been reacted with phenolic compounds of various types to produce condensation products which are useful in a number of applications including the treatment of various natural fibers. The art does not disclose, however, that dialdehyde starch and meta-hydroxyaromatic compounds may be caused to condense on and react with the hair fibers to produce a cosmetically useful hair setting effect.

The hydroxyaromatic compounds which we have found to be useful in the practice of this invention are the benzene and naphthalene derivatives having two hydroxyl groups which are meta(1,3) to each other. Examples of such materials are gallic acid; 3,5-dihydroxybenzoic acid; orcinol; 1,3-dihydroxynpahthalene and, our preferred material, resorcinol.

In preparing the compositions of this invention, we have found that ratios of dialdehyde polysaccharide to hydroxyaromatic compound may range from 1:0.75 to 1:2.0 by weight, preferably 1:1 to 1:1.5. While a wide range of concentrations of mixtures containing the two active materials in water may be used in effectively setting the hair, we have found that from 2-8% by weight of combined dialdehyde polysaccharide and hydroxyaromatic compound may be used for favorable cosmetic hair attributes. We prefer to use 3.5% to 5.0%.

The compositions of this invention may be applied to the hair in a variety of ways prior to the application of the heat necessary to bring about the condensation polymerization referred to hereinbefore.

In one mode of application, an appropriate quantity of treating material is applied along the length of tresses of dry hair by means of spray application after which the tresses are combed from top to bottom to distribute the treating composition. Alternatively, tresses of hair may be shampooed, rinsed, and towel blotted to remove excess water after which an appropriate quantity of a composition is applied along the length of each tress from a squeeze-bottle or the like after which the tresses are combed through.

Following application of the treating composition, the hair is dried and curled by using a conventional heated rod or bursh curling appliance or other conventional heat source with the time of treatment depending upon the temperature of the heat source employed. We have found that temperature ranges of 40°–150° C., preferably 50°–120° C. may be employed. When a curling iron having a rod surface temperature approaching 100° C. is employed, it will only be necessary to apply the heat for about 10 seconds to bring about the condensation reaction between the reactive materials. On the other hand, when a lower temperature is used as, for example, a hair dryer having an air temperature of 40°–50° C., it may be necessary to allow the hair to remain in its wrapped condition for up to an hour to assure complete drying and reaction.

Where it is intended to employ the compositions of this invention in setting hair which has been bleached or oxidatively colored, it is desirable to include a hair conditioning ingredient to enhance ease of combing, both during the application of the composition and while styling the set hair after heat treatment. Such conditioning agents include proteins, surfactants and materials which can be broadly classified as oils and waxes. The use of such materials is well known to those skilled in the art of formulation of hair treating compositions and is described in, for example, the treatise entitled *Cosmetics-Science and Technology*, Second Edition, Vol. 2, pages 345–372, Edited by M. S. Balsam and Edward Sagarin. These materials may be incorporated in amounts ranging from 0.05 to 1.0% by weight of the total composition.

EXAMPLE I

A solid dialdehyde starch derived from cornstarch and having a degree of oxidation of 90-100% (SUMSTAR-190; Hexcel Corp.) is purified by stirring a dispersion of 150 grams of the solid starch and 3000 ml of distilled water for 3-4 hours and filtering. The process is repeated until the pH of the water reaches 5.15, after which the filtered material is vacuum oven-dried and bottled for further use.

The purified starch is hydrated for use in the practice of the invention by dispersing 10 grams of the material in 100 ml of distilled water containing 1.0 gram sodium tetraborate (borax) which has been heated to 60° C. The temperature is raised to 80°-85° C. and held until a clear liquid dispersion results after approximately 15 minutes. The dispersion is cooled and bottled for future use.

An aqueous dispersion of purified, hydrated dialdehyde starch and resorcinol having a total solids content of 4.8% by weight and a starch dialdehyde:resorcinol molar ratio of 1.0:1.5 is applied to one side of the head of a female subject having hair approximately six inches long which has been shampooed with a commercially available anionic shampoo, rinsed and towel dried. After approximately 20 ml. of the above composition has been distributed even through one side of the hair by combing, the entire head is partially dried using a home style, hot air blower dryer after which the hair on both sides of the head is set using a commercially available heated rod curling iron having a rod surface temperature of about 100° C. After styling both sides of the head, results are compared for body, feel, luster, and combing ease. The composition of this invention imparts more body and luster to the treated side than was present in the control side. Combing ease on the treated side is rated as better than average and reduced flyaway is observed. Twenty-four hours after the treatment, the treated side is judged to have better set holding and body.

EXAMPLE II

A composition as described in Example I is prepared containing, in addition, 0.5% by weight of stearyldimethylbenzyl ammonium chloride as a hair conditioning agent.

After application of the composition as described in Example I, the hair is set on mesh rollers having a diameter of 1 inch, after which it is dried under a salon-style hair dryer having an air flow temperature of about 45° C. After about 40 minutes, the rollers on both sides of the head are removed and the hair styled. Comparative evaluation of the two sides produces the same results as described in Example I.

EXAMPLE III

A composition as described in Example I is prepared except that 3,5-dihydroxybenzoic acid is substituted in place of the resorcinol.

The composition is applied to the head of the subject as described in Example I except that the hair of the subject is allowed to dry completely before application. After application, excess water from the solution is allowed to evaporate under ambient conditions until the hair is nearly dry after which it is curled by the use of a conventional heated rod curling iron as described in Example I. Comparison of the two sides yields results as described in Example I.

While particular embodiments of the invention have been described, it will be apparent to those skilled in the art that variations may be made thereto without departing from the spirit of the invention and the scope of the appended claims.

What is claimed is:

1. A composition for setting hair comprising an aqueous dispersion containing a hydrated dialdehyde polysaccharide having a molecular weight of from about 10,000 to about 50,000 and a hydroxyaromatic compound selected from the group consisting of reactive derivatives of benzene or naphthalene having hydroxy groups which are meta(1,3) to each other, the ratio by weight of said dialdehyde polysaccharide and said hydroxyaromatic compound being from about 1:0.75 to about 1:2.0, the quantity of said aldehyde polysaccharide and said hydroxyaromatic compound being about 2 to about 8% by weight of the total composition.

2. A composition for setting hair as described in claim 1 in which the dialdehyde polysaccharide is dialdehyde starch.

3. A composition for setting hair as described in claim 1 in which said hydroxyaromatic compound is selected from the group consisting of gallic acid; 3,5-dihydroxybenzoic acid; orcinol; 1,3-dihydroxynaphthalene; and resorcinol.

4. A composition for setting hair as described in claim 1 and also containing from about 0.05 to about 1.0% by weight of the total of a hair conditioning ingredient selected from the group consisting of proteins, surfactants, oils, and waxes.

5. A method for setting hair comprising application of a composition as described in claim 1 followed by heating the hair to a temperature of 40°-150° C. for at least 10 seconds, until a condensation reaction between said dialdehyde polysaccharide and said hydroxyaromatic compound takes place.

* * * * *